(12) United States Patent
Wang et al.

(10) Patent No.: US 7,465,311 B2
(45) Date of Patent: *Dec. 16, 2008

(54) CATHETER HAVING AN IMPROVED DISTAL TIP

(75) Inventors: Edwin Wang, Tustin, CA (US);
Roseminda J. White, Wildomar, CA (US); Jeong S. Lee, Temecula, CA (US); Tim Kitchen, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 499 days.

This patent is subject to a terminal disclaimer.

(21) Appl. No.: 11/172,543

(22) Filed: Jun. 29, 2005

(65) Prior Publication Data
US 2005/0240214 A1    Oct. 27, 2005

(51) Int. Cl.
*A61M 29/00* (2006.01)

(52) U.S. Cl. .................................................... 606/194
(58) Field of Classification Search ......... 606/191–199; 604/96.01, 97.01, 101.01, 101.02, 101.03, 604/102.01, 103.06, 103.12
See application file for complete search history.

(56) References Cited

U.S. PATENT DOCUMENTS

| 5,458,615 | A | 10/1995 | Klemm et al. | |
|---|---|---|---|---|
| 5,662,703 | A | 9/1997 | Yurek et al. | |
| 6,344,029 | B1 * | 2/2002 | Estrada et al. | 604/103.09 |
| 6,344,045 | B1 | 2/2002 | Lim et al. | |

* cited by examiner

*Primary Examiner*—Kevin T Truong
(74) *Attorney, Agent, or Firm*—Fulwider Patton LLP

(57) ABSTRACT

An elongated balloon catheter having a distal tip member on the distal end of the catheter and having a sleeve surrounding and secured at least to the proximal end of the distal tip member.

15 Claims, 2 Drawing Sheets

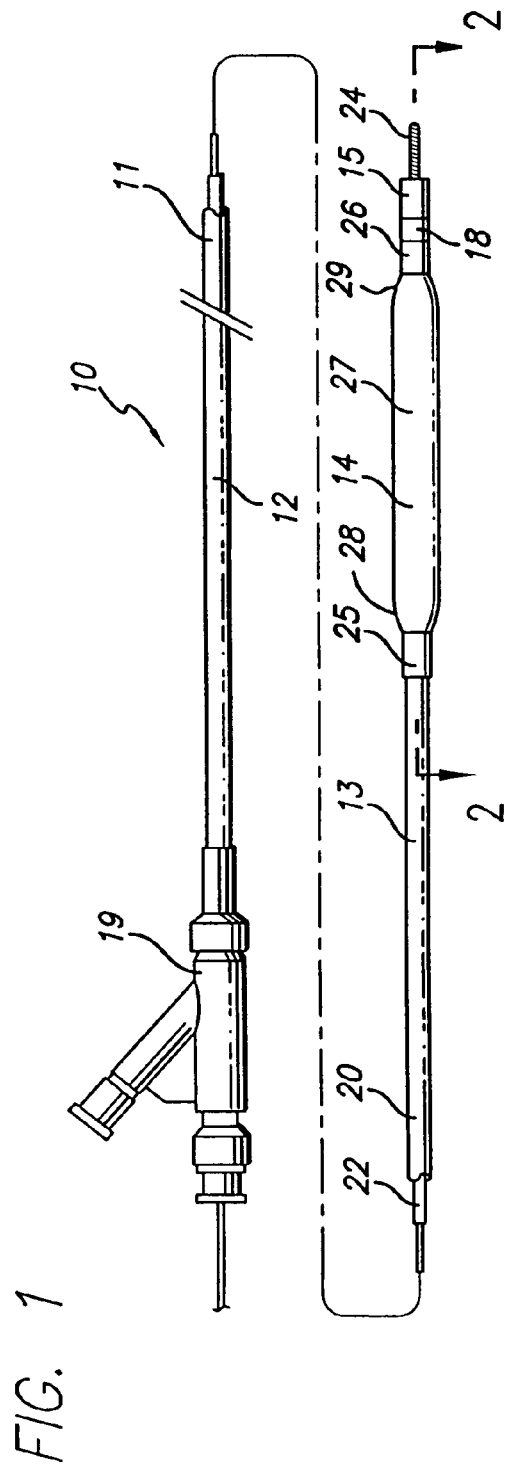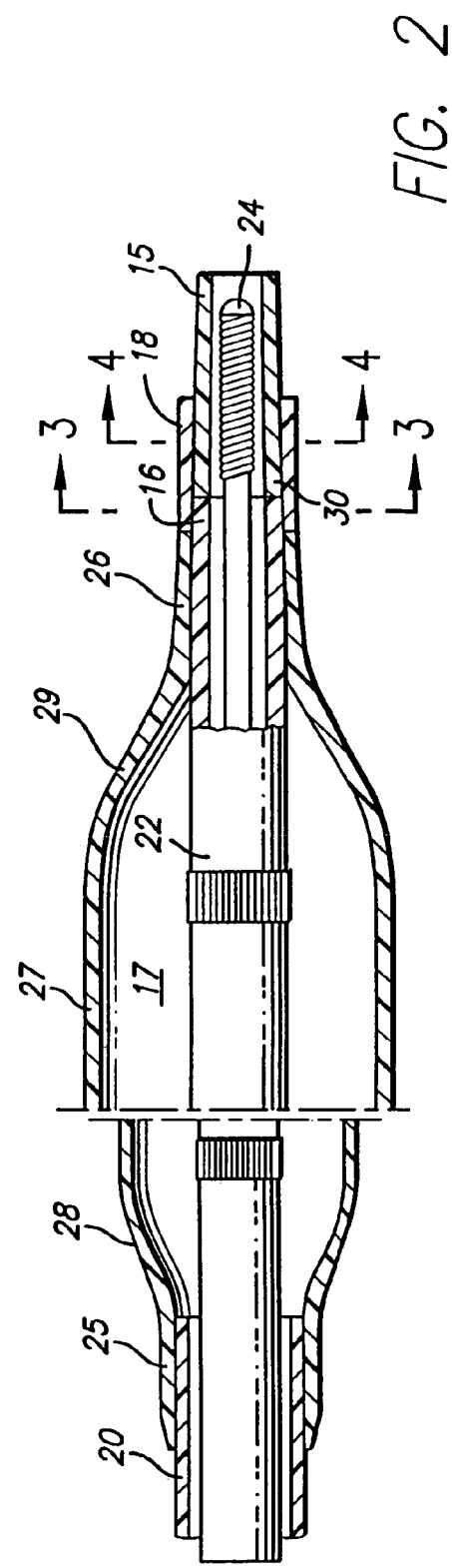

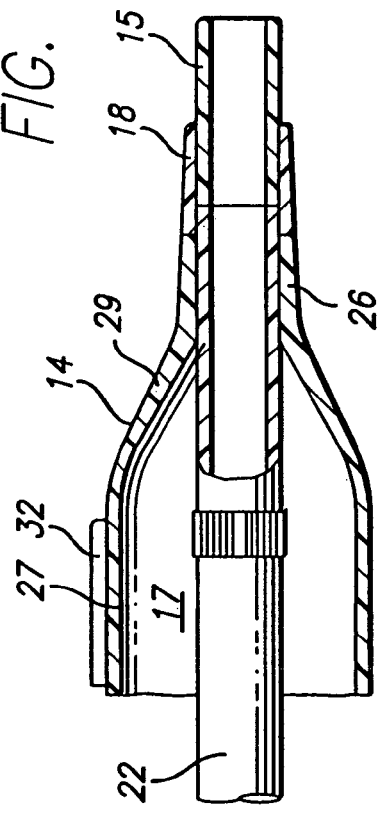
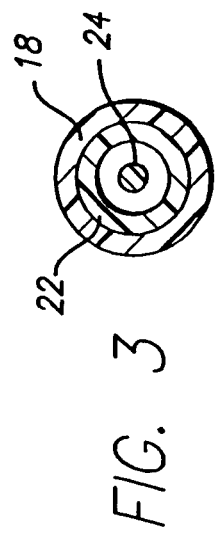
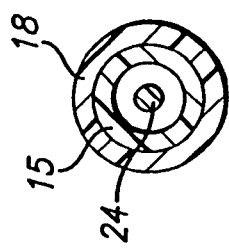
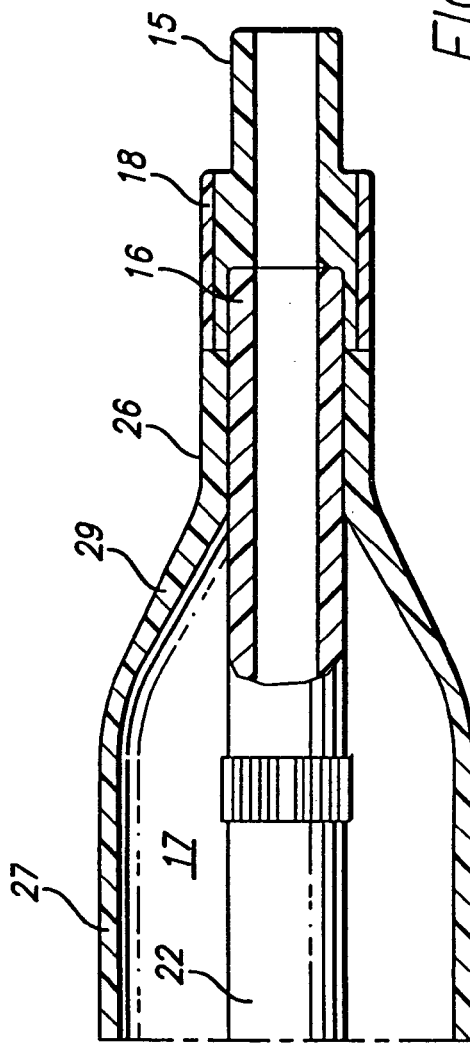

CATHETER HAVING AN IMPROVED DISTAL TIP

FIELD OF INVENTION

This invention generally relates to medical devices, and particularly to intraluminal balloon catheters having improved distal tips.

BACKGROUND OF THE INVENTION

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion.

Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

Catheters designed for intravascular procedures such as angioplasty have a number of design considerations. Such catheters must be able to transmit force along the length of the catheter shaft so that the catheter can be pushed through the patient's vasculature. However, the catheter shaft must also have sufficient flexibility to allow the catheter to track over a guidewire through tortuous vasculature as well as crossing stenosed portions of the vascular anatomy.

Prior art intravascular catheters have commonly included a soft distal tip to prevent or minimize injury to the vessel during advancement of the catheter therein. One difficulty has been forming a connection between the soft tip and the catheter which is sufficiently strong to prevent disengagement of the soft tip or kinking at the junction between the soft tip and catheter shaft. Additionally, it is necessary to balance the strength of the connection between the soft tip and the catheter shaft with the need to minimize the stiffness of the distal end of the catheter. Minimizing the stiffness of the distal end of the catheter results in improved maneuverability of the catheter.

Accordingly, it would be a significant advance to provide a catheter with a soft tip having improved performance. This invention satisfies these and other needs.

SUMMARY OF THE INVENTION

The present invention is directed to a balloon catheter with improved distal extremity. The catheter includes an elongated catheter shaft having a proximal end, a distal end, and proximal and distal shaft sections. A guidewire receiving lumen extends along at least a distal portion of the catheter shaft to a port provided at the distal end of the catheter shaft. An inflation lumen extends along at least a portion of the catheter shaft terminating at a point proximal to the distal end of the catheter shaft.

An inflatable member, such as a balloon with proximal and distal ends and an interior chamber, is disposed on the distal catheter shaft section. The interior chamber of the balloon is in fluid communication with the inflation lumen extending within the catheter shaft. The balloon further includes a distal shaft portion or skirt which is sealingly secured to the portion of the catheter shaft extending through the interior chamber of the balloon. The catheter has a soft tip member which is secured to the distal end of the portion of the catheter extending through the interior of the balloon and which has an inner lumen which is in fluid communication with the guidewire receiving lumen of the catheter shaft. A polymeric sleeve is secured to the proximal end of the soft tip member and may also be secure to a distal end of the portion of the catheter shaft which extends beyond the distal end of the distal balloon shaft. The sleeve may be heat or fusion bonded or adhesively bonded, preferably by a UV-curable adhesive to the underlying member or members.

A balloon catheter having features of the invention exhibits improved tensile characteristics with excellent flexibility.

These and other advantages of the invention will become more apparent from the following detailed description when taken in conjunction with the accompanying exemplary drawings.

BRIEF DESCRIPTION OF THE DRAWINGS

FIG. 1 is an elevational view, partially in section, of a balloon catheter embodying features of the invention.

FIG. 2 is an enlarged elevational view, partially cutaway, of the distal portion of the catheter shown in FIG. 1.

FIG. 3 is a transverse cross-section of the catheter of FIG. 2 taken along lines 3-3.

FIG. 4 is a transverse cross-section of the catheter of FIG. 2 taken along lines 4-4.

FIG. 5 is an elevational view partially in section of an alternative embodiment in which the outer sleeve on the distal tip is tapered in the distal direction to smaller transverse dimensions.

FIG. 6 is a partial longitudinal cross-sectional view of an alternative design of the distal tip of the catheter shown in FIG. 1.

DETAILED DESCRIPTION OF THE INVENTION

FIGS. 1 through 4 illustrate a balloon catheter 10 embodying features of the invention, which include an elongated catheter shaft 11 having proximal and distal shaft sections 12 and 13 respectively, an inflatable balloon 14 on the distal catheter shaft section and a distal tip member 15 secured to the distal end 16 of a portion of the catheter shaft that extends through the interior chamber 17 of the balloon 14. A flexible sleeve 18 is secured to the exterior of the distal end 16 and the distal tip member 15. An adapter 19 is provided on the proximal shaft section 12 for directing inflation fluid, and the like to and from the catheter 10.

In the embodiment best illustrated in FIGS. 2-4, the distal shaft section 13 has an outer tubular member 20 with an inflation lumen 21 extending therethrough, and an inner tubular member 22 with a guidewire receiving lumen 23 disposed within the inflation lumen 21 for slidably receiving a guidewire 24. Balloon 14 has proximal balloon shaft section or skirt 25 and a distal balloon shaft section or skirt 26 and a cylindrical working section 27. Proximal and distal tapers 28 and 29 respectively extend from the ends of the working section 27 to the balloon shaft sections 25 and 26 as shown. The inner tubular member 22 extends through the balloon interior 17 and has distal end 15 which extends through the distal balloon shaft section and preferably slightly beyond thereof.

The proximal balloon shaft section 25 is sealingly secured to the distal end of outer tubular member 20 and the distal balloon shaft section 26 is sealingly secured to the distal portion 27 of the inner tubular member 22. Sleeve 18 is secured to the distal end 16 of the inner tubular member 22 which extends beyond the distal end of the balloon distal shaft section 26 and the proximal end 30 of distal tip member 15. The distal tip member 15 has an inner lumen which forms in part the guidewire lumen 23 and is preferably has the same inner diameter as the portion of the guidewire lumen 23 within the inner tubular member 22.

FIG. 5 illustrates an alternative design of the distal extremity of the catheter 10 wherein the distal tip member 15 and the sleeve 18 taper in the distal direction to smaller transverse dimensions. A stent 32 is shown mounted on the exterior of the balloon working section 27.

FIG. 6 illustrates an alternative catheter construction wherein the distal tip member 15 has a proximal portion which extends over the distal end 16 of the inner tubular member 22. In this embodiment the sleeve 18 is secured only to the exterior of the distal tip member 15, but the sleeve 18 extends over the portion of the distal end 16 of the inner tubular member 22 which extends beyond the end of the distal balloon shaft section 26. The sleeve 18 and distal tip member 15 may be coextruded together, preferably from compatible polymeric materials to form a single tubular member. The outer layer forming the sleeve 18 may be removed by suitable means from the exterior distal portion of the tubular member and the inner portion may be removed from the proximal portion to facilitate mounting over the distal end 16.

In one catheter design embodying features of the invention, the distal tip member 15 has a length of about 1 to about 10 mm, preferably about 2.5 to about 5 mm and typically about 2.5 to about 3.5 mm. The length of sleeve 18 should range from about 1 to about 10 mm; preferably about 1 to about 5 mm and typically about 1.5 to about 2.5 mm. The distal end 16 of the catheter shaft 11 (or inner tubular member 22) may be flush with the distal end of the distal balloon shaft section 26 or extend distally from the distal end of the distal balloon shaft section 26 a distance not more than about 20 mm, preferably not more than about 10 mm. Typically, the distal end 16 will extend about 0.25 to about 0.5 mm from the distal balloon shaft section.

The distal tip member 15, has a wall thickness ranging from about 0.0025 to about 0.005 inch (0.06-0.13 mm), preferably, from about 0.003 to about 0.004 inch (0.08-0.1 mm), The sleeve 18 may have a wall thickness of about 0.0015 to about 0.005 inch (0.04-0.13 mm), preferably about 0.002 to about 0.003 inch (0.05-0.08 mm).

The dimensions of balloon catheter 10 are determined largely by the size of the artery or other body lumen through which the catheter must pass or the size of the stent being delivered. Typically, the outer tubular member 20 has an outer diameter of about 0.02 to about 0.045 inch (0.5 to 1.1 mm), typically about 0.037 inch (0.94 mm), an inner diameter of about 0.015 to about 0.035 inch (0.38 to 0.89 mm), typically about 0.03 inch (0.76 mm). The wall thickness of the outer tubular member 20 can vary from about 0.002 to about 0.008 inch (0.051 to 0.201 m), typically about 0.003 inch (0.076 mm). The inner tubular member 22 typically has an outer diameter of about 0.016 to about 0.03 inch (0.4-0.8 mm), typically about 0.021 inch (0.5 mm). The overall working length of the catheter 10 may range from about 100 to about 150 centimeters (cm), and is typically about 147 cm. Preferably, balloon 14 may have a working length about 0.5 cm to about 4 cm and typically about 2 cm with an inflated working diameter of about 1 to about 8 mm, and for coronary applications about 1 mm to about 5 mm. The cylindrical wall forming the working length 27 of the balloon 14 has a thickness ranging from about 0.001 to about 0.003 inch (0.03-0.08 mm), preferably, from about 0.0015 to about 0.002 inch (0.04-0.05 mm).

The dimensions, such as wall thickness, of the various catheter components may vary depending upon the strength and flexibility characteristics of the material from which the catheter components are formed. Moreover, the wall thickness of the catheter components may also vary, if they are tapered such as the distal tip member and sleeve shown in FIG. 5.

The various catheter components can be formed of suitable conventional materials. The inner tubular member and outer tubular member, are preferably formed of material, or include material thereon, which is compatible with the balloon material to allow formation of appropriate bonding therebetween. Similarly, the sleeve and the distal tip member are preferably formed of compatible materials for essentially the same reason.

In one design embodying features of the invention, the distal tip member 15 is of a soft tip design configured to provide an atraumatic distal end on the catheter to minimize injury to the patient's vasculature during advancement of the catheter therein. The distal tip member and sleeve are preferably formed of a polymeric material having a Shore durometer hardness of about 80A to about 90D, preferably about 40D to about 75D. Suitable materials include PEBAX (a polyether block amide) or PELLETHANE (a polyurethane). The Shore hardness of the sleeve 18 may be less than or greater than the Shore hardness of the distal tip member 15, but preferably is less, e.g. with PEBAX the Shore hardness may be 40D for the sleeve 18, verses 55D for the distal tip member 15. However, the distal tip member may be formed of a variety of polymeric materials including polyethylene based adhesives such as PRIMACOR, high density polyethylene (HDPE), polyurethane, and polyesters such as HYTREL. However, the choice of material depends on a variety of factors including the desired application and the method used to make the distal tip member 15 and the sleeve.

To the extent not discussed herein, the various catheter components can be formed of conventional materials. Outer tubular member 20 and the inner tubular member 22 can be formed by conventional techniques, for example by extruding, from materials already found useful in intravascular catheters such a polyethylene, polyvinyl chloride, polyesters, polyamides, polyimides, polyetherether ketone (PEEK) and composite or blends of these materials. The various components may be joined by heat or fusion bonding or use of suitable adhesives, particularly UV cured adhesives.

A variety of balloon catheter designs may be used, including rapid exchange, over-the-wire, and fixed wire catheter designs. A rapid exchange catheter generally includes a distal guidewire port in the distal end of the catheter shaft, a proximal guidewire port spaced a substantial distance distal to the proximal end of the catheter shaft and at least about 4, preferably at least 10 cm from the distal end of the catheter, and a guidewire lumen extending between and in fluid communication with the proximal and distal guidewire ports. As illustrated in FIG. 5, the balloon catheter of the invention may be used to deliver prostheses, such as expandable stents, grafts, and the like, to a desired location within the patient's vasculature. The stent 32, schematically shown in FIG. 5, comprises an expandable tubular body, typically having an openwalled structure, which is mounted on balloon 34 so that upon inflation of the balloon the stent will be expanded and seated against the interior of the vessel wall. Additionally, catheter 10 may be used to touch up a previously implanted stent by positioning balloon within a stent lumen and expanding the balloon to further expand the stent within a body lumen.

While particular designs embodying features of the invention have been illustrated and described herein, it will be apparent to those skilled in the art that various modifications can be made to the invention. Moreover, those skilled in the art will recognize that feature found in one embodiment may be utilized in another embodiment. Terms such as "elements", "members", "devices" and words of similar import when used herein shall not be construed as invoking the provisions of 35 U.S.C. §112(6) unless the following claims expressly use the term "means" or "step" followed by a particular function.

Accordingly, it is not intended that the invention be limited, except as by the appended claims.

What is claimed is:

1. A balloon catheter, comprising:
  a. an elongated catheter shaft which has a proximal catheter shaft section, a distal catheter shaft section, an inflation lumen, a guidewire receiving lumen extending along at least a portion of the distal shaft section in communication with a guidewire distal port at the distal end of the catheter, and a balloon on the distal catheter shaft section having an interior in fluid communication with the inflation lumen of the shaft, and having an inflatable section, and proximal and distal balloon skirt sections secured to the catheter shaft;
  b. a distal tip member mounted on and bonded to an outer surface of the distal catheter shaft section, which has a proximal section with a proximal portion forming a lap joint over the distal end of the catheter shaft, a distal section located distal to the distal end of the shaft having a distal end defining the guidewire distal port, and an inner lumen in fluid communication with the guidewire receiving lumen of the shaft; and
  c. a polymeric sleeve which has a proximal end, and a distal end, and which is disposed about and secured to the proximal section of the distal tip member so that the distal end of the sleeve is located distal to the catheter shaft distal end and proximal to the distal tip distal end, and the proximal end of the sleeve is located proximal to the catheter shaft distal end, and the sleeve extends distally without tapering so that the distal end of the sleeve has the same outer diameter as the proximal end of the sleeve.

2. The balloon catheter of claim 1 wherein the distal section of distal tip member has a smaller outer diameter than the distal tip member proximal section.

3. The balloon catheter of claim 1 wherein the proximal end of the distal tip member abuts and has a smaller outer diameter than a distal end face of the balloon distal skirt section.

4. The balloon catheter of claim 3 wherein the proximal end of the sleeve abuts the distal end face of the balloon distal skirt section, so that the sleeve proximal end and the distal tip member proximal end are radially aligned.

5. The balloon catheter of claim 3 wherein the shaft distal end is located distal to the distal end of the balloon distal skirt section.

6. The balloon catheter of claim 1 wherein the sleeve is formed of material which is compatible with material of which the distal tip member is formed.

7. The balloon catheter of claim 6 wherein the sleeve and distal tip member comprise a coextruded tube.

8. The balloon catheter of claim 6 wherein the sleeve is formed of a polymeric material selected from the group consisting of polyether block amide and polyurethane.

9. The balloon catheter of claim 1 wherein the sleeve is formed of a polymeric material having a Shore hardness between about 80A and 90D.

10. The balloon catheter of claim 1 wherein the sleeve is formed of a polymeric material having a Shore hardness between about 40D and 65D.

11. The balloon catheter of claim 1 wherein the distal tip member is formed of a polymeric material having a Shore hardness between about 80A and 90D.

12. The balloon catheter of claim 1 wherein the distal tip member is formed of a polymeric material having a Shore hardness between about 40D and 65D.

13. The catheter of claim 1 wherein the distal tip member is formed of a polymeric material selected from the group consisting of a polyether block amide, a polyester, a polyethylene based adhesives, high density polyethylene, polyurethane.

14. The catheter of claim 2 wherein the distal tip member outer diameter steps down from the proximal to the distal section of the distal tip member forming a step change with a face perpendicular to a longitudinal axis of the distal tip member, and the distal end of the sleeve is radially aligned with the step change in the outer diameter of the distal tip member.

15. A balloon catheter, comprising:
  a. an elongated catheter shaft which has a proximal catheter shaft section, a distal catheter shaft section, an inflation lumen, a guidewire receiving lumen extending along at least a portion of the distal shaft section in communication with a guidewire distal port at the distal end of the catheter, and a balloon on the distal catheter shaft section having an interior in fluid communication with the inflation lumen of the shaft, and having an inflatable section, and proximal and distal balloon skirt sections secured to the catheter shaft;
  b. a distal tip member mounted on and bonded to an outer surface of the distal catheter shaft section, having an inner lumen in fluid communication with the guidewire receiving lumen of the shaft, a proximal section with a proximal portion forming a lap joint over the distal end of the catheter shaft, and a distal section which has the same polymeric composition as the proximal section, which is located distal to the distal end of the shaft, and which has a distal end defining the guidewire distal port; and
  c. a polymeric sleeve which has a proximal end, and a distal end, and which is disposed about and secured to the proximal section of the distal tip member so that the distal end of the sleeve is located distal to the catheter shaft distal end and proximal to the distal tip distal end, and the proximal end of the sleeve is located proximal to the catheter shaft distal end.

* * * * *

UNITED STATES PATENT AND TRADEMARK OFFICE
CERTIFICATE OF CORRECTION

PATENT NO.       : 7,465,311 B2                                            Page 1 of 1
APPLICATION NO.  : 11/172543
DATED            : December 16, 2008
INVENTOR(S)      : Edwin Wang et al.

It is certified that error appears in the above-identified patent and that said Letters Patent is hereby corrected as shown below:

Title Page, insert --Related U.S. Application Data--
Item --(60) Continuation of application No. 10/002,613, filed on Nov. 1, 2001, now Pat. No. 6,918,920--.

Signed and Sealed this

Seventh Day of April, 2009

JOHN DOLL
*Acting Director of the United States Patent and Trademark Office*